United States Patent
Subramaniam

[19]

[11] Patent Number: 5,914,115
[45] Date of Patent: Jun. 22, 1999

[54] BIOCOMPATIBLE COATING, MEDICAL DEVICE USING THE SAME AND METHODS

[75] Inventor: Raj Subramaniam, Fremont, Calif.

[73] Assignee: Surface Genesis, Inc., Menlo Park, Calif.

[21] Appl. No.: 08/453,270

[22] Filed: May 30, 1995

Related U.S. Application Data

[62] Division of application No. 08/324,413, Oct. 17, 1994, Pat. No. 5,643,580.

[51] Int. Cl.$^6$ .......................... A61L 33/00; A61K 41/00; B05D 3/06
[52] U.S. Cl. .................... 424/400; 427/535; 210/500.24; 428/936
[58] Field of Search ...................... 424/400; 427/535–37, 427/238; 210/500.24; 428/936

[56] References Cited

U.S. PATENT DOCUMENTS

| | | |
|---|---|---|
| 3,754,555 | 8/1973 | Schmitt .................................... 128/418 |
| 4,326,932 | 4/1982 | Hammar . |
| 4,973,493 | 11/1990 | Guire . |
| 4,979,959 | 12/1990 | Guire . |
| 5,002,582 | 3/1991 | Guire et al. . |
| 5,102,798 | 4/1992 | Giuseppi-Elie . |
| 5,132,108 | 7/1992 | Narayanan et al. ................. 424/78.17 |
| 5,217,492 | 6/1993 | Guire et al. . |
| 5,244,654 | 9/1993 | Narayanan . |
| 5,258,041 | 11/1993 | Guire et al. . |
| 5,263,992 | 11/1993 | Guire . |
| 5,324,647 | 6/1994 | Rubens et al. . |
| 5,336,518 | 8/1994 | Narayanan et al. . |

*Primary Examiner*—Edward J. Webman
*Attorney, Agent, or Firm*—Flehr Hohbach Test Albritton & Herbert LLP

[57] ABSTRACT

The invention involves using a glow discharge plasma to functionalize a surface of medical devices such as catheters, particularly intracardial catheters, with covalently bound thermochemically reactive groups. The surface is further contacted with a bioactive agent, particularly antithrombogenic coatings, which is thermochemically covalently coupled to the reactive group to form a therapeutically effective coating. The selected bioactive agent is then covalently bound to the surface by thermochemical reaction with the surface reactive groups. In another embodiment, the functionalizing step comprises contacting the surface with a Langmuir-Blodgett film comprising an amphipathic compound and a bioactive agent and using a plasma to covalently crosslink the Langmuir-Blodgett film to the medical device surface and to the bioactive agent. Medical devices prepared by the subject methods are also provided.

7 Claims, 6 Drawing Sheets

STENT 5,914,115

BIOCOMPATIBLE COATING, MEDICAL DEVICE USING THE SAME AND METHODS

This is a division of application Ser. No. 08/324,413 filed Oct. 17, 1994, now U.S. Pat. No. 5,643,580.

The Field of the invention is biocompatible coatings of medical devices, particularly antithrombogenic coatings for intravascular catheters.

Medical devices which have direct contact with blood flow have a tendency to promote localized thrombosis. Additionally, it is often desirable to promote localized thrombosis at the sites of wounds. The present invention provides novel methods for applying therapeutic coatings such as thrombogenic and antithrombogenic coatings to a variety of medical devices.

SUMMARY OF THE INVENTION

The invention provides covalently attached therapeutic coatings for surfaces of medical devices and a variety of methods for making medical devices with such coatings.

In one embodiment, the methods involve functionalizing a surface of the medical device with covalently bound thermochemically reactive groups. The surface is further contacted with a bioactive agent which is thermochemically covalently coupled to the reactive group to form a therapeutically effective coating. In a preferred embodiment, the functionalizing step comprises contacting the surface with a plasma to form the thermochemically reactive groups. A wide variety of reactive groups which provide convenient reactants for the selected bioactive agent may be used. The selected bioactive agent is then covalently bound to the surface by thermochemical reaction with the surface reactive groups.

In another embodiment, the functionalizing step comprises contacting the surface with a Langmuir-Blodgett film comprising an amphipathic compound and a bioactive agent. A plasma or thermochemical means are then used to covalently crosslink the Langmuir-Blodgett film to the medical device surface and to the bioactive agent. Optionally, in this embodiment, the surface may also be functionalizing with a first thermochemically reactive group capable of reacting with at least one of the amphipathic compound and the bioactive agent. Similarly, the bioactive agent may be derivatized with a second reactive group capable of reacting with the first reactive group.

In these methods, the bioactive agent is advantageously derivatized with a label capable of providing a detectable signal. Hence the detectable signal is used to quantify the bound bioactive agent on the device's surface.

Where the bioactive agent is antithrombogenic, it may be a relatively irreversible thrombin inhibitor, such as D-Phe-Pro-Arg-chloromethyl ketone, or a relatively reversible thrombin inhibitor, such as heparin or a polypeptide comprising the amino acid sequence Ile-Pro-Glu-Glu-Tyr-Leu-Gln.

Exemplary medical devices for antithrombogenic coatings include catheters, particularly intracardial catheters, vascular stents and grafts and various blood transfer devices such as blood oxygenators, dialysis and plasmapheresis devices, etc. Exemplary medical devices for thrombogenic coatings include wound closing and wound covering devices such as sutures, bandages, etc.

The medical devices of the invention have a surface with a covalently attached dry therapeutic coating. In one embodiment, the coating comprises thermochemically reactive groups covalently bound to the surface and a bioactive agent covalently bound to a portion but fewer than all of the thermochemically reactive groups. In another embodiment, the coating comprises a Langmuir-Blodgett film comprising an amphipathic compound and a bioactive agent, where the amphipathic compound is covalently crosslinked to the surface, and the bioactive agent is covalently crosslinked to the amphipathic compound.

The invention also provides general methods for treating a surface of a medical device with a therapeutic covalent coating of a bioactive agent; thereafter, washing the surface to remove any bioactive agent which is not covalently bound; thereafter, causing a reagent capable of selectively, non-covalently binding to the bioactive agent to become selectively and noncovalently bound to the bioactive agent; thereafter, washing the surface to remove any of such reagent which is not selectively bound to the bioactive agent; thereafter, detecting a radiative signal at an intensity which meets or exceeds a predetermined intensity which correlates with the presence of coating of a predetermined amount of the bioactive agent covalently bound to the surface. For example, the reagent may be a specific antibody and the signal fluorescence.

DESCRIPTION OF THE DRAWINGS

FIG. 1 shows a typical plasma chamber.
FIG. 2 shows a typical plasma surface modification system.
FIG. 3 shows a catheterized heart.
FIG. 4 shows a typical electrophysiology catheter.
FIG. 5 shows a typical stent.
FIG. 6 shows a typical blood oxygenator.

DETAILED DESCRIPTION OF THE INVENTION

Figure 1:
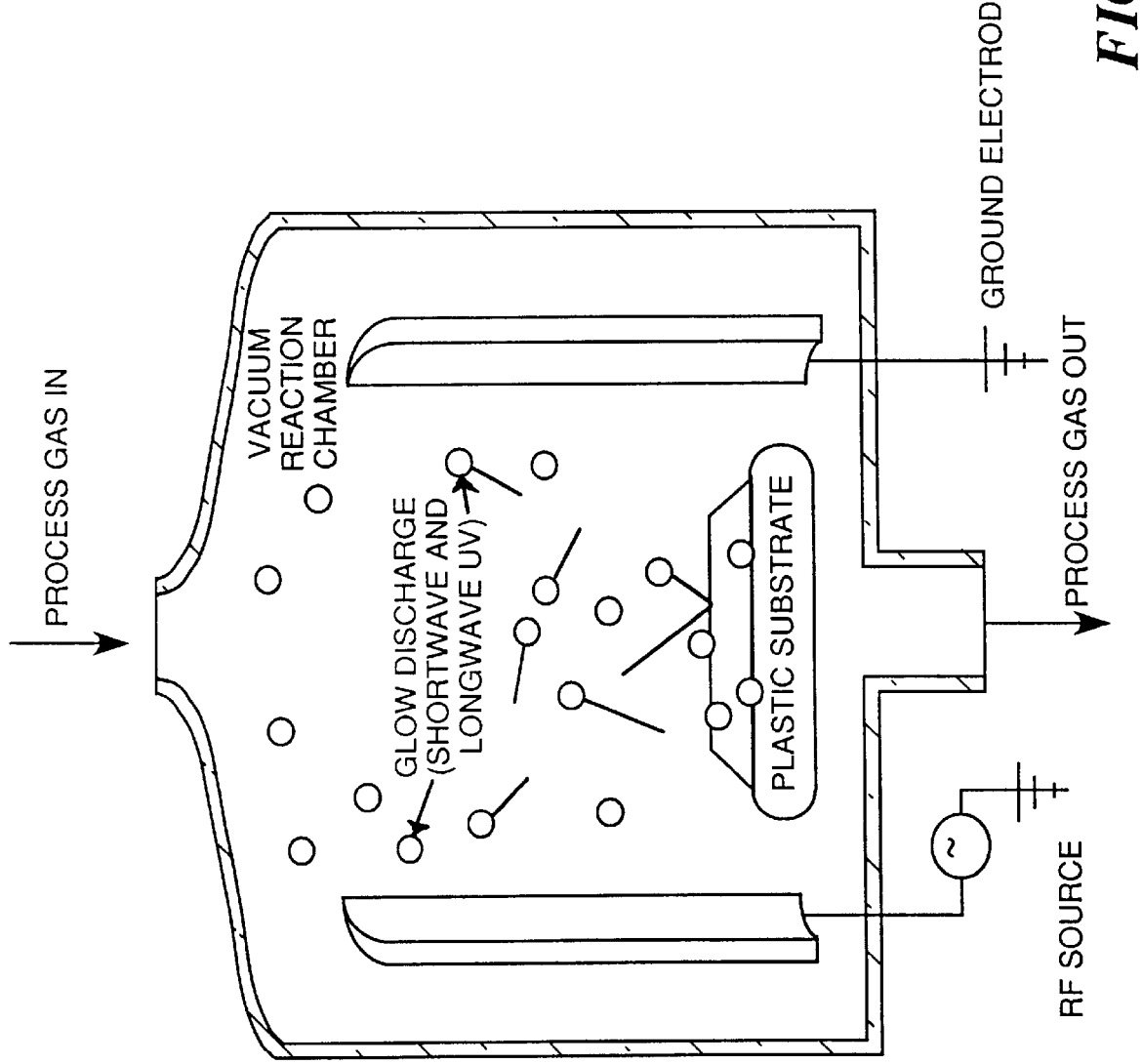
FIG. 1.
Figure 2:
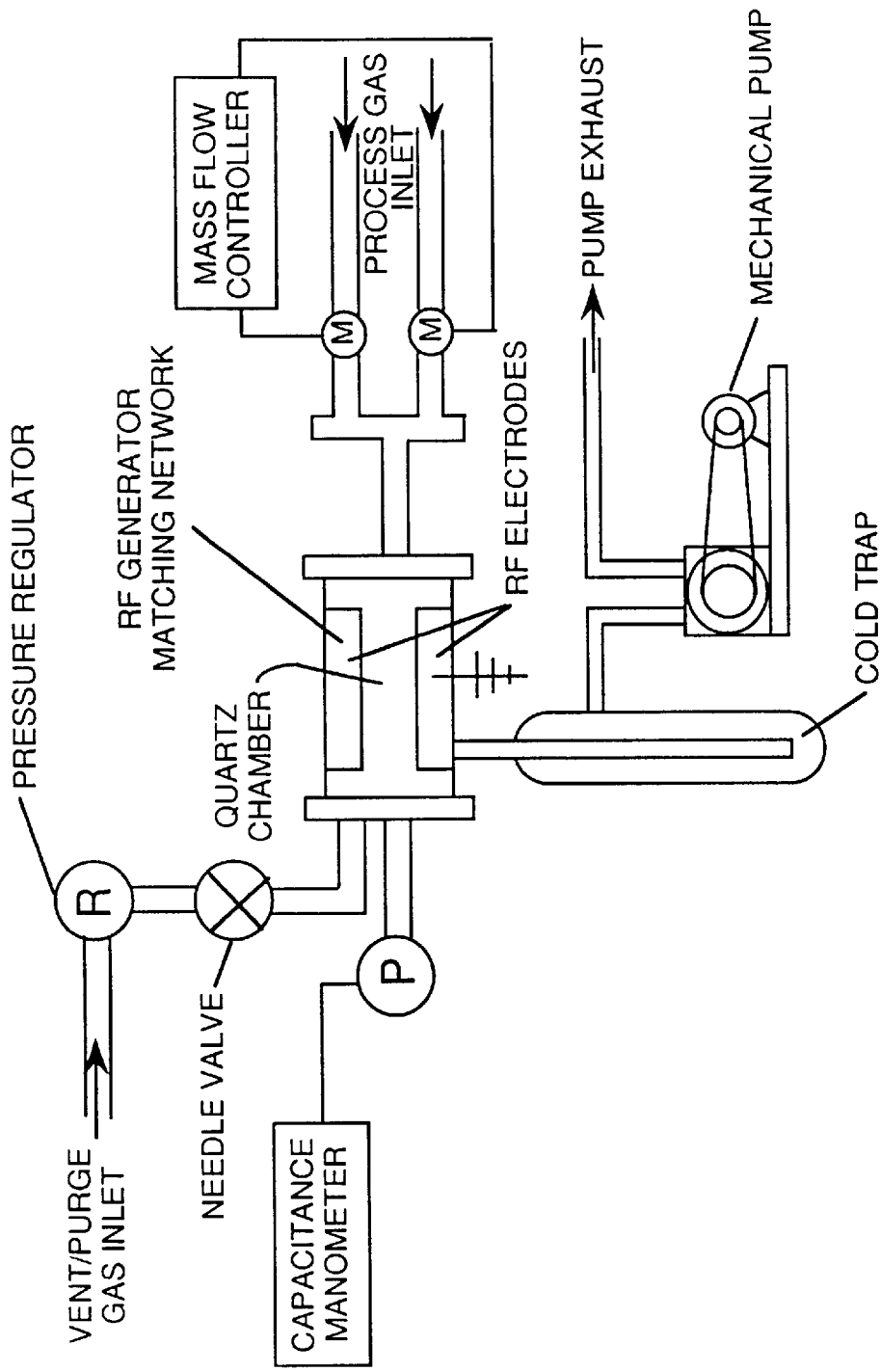
FIG. 2.
Figure 3:
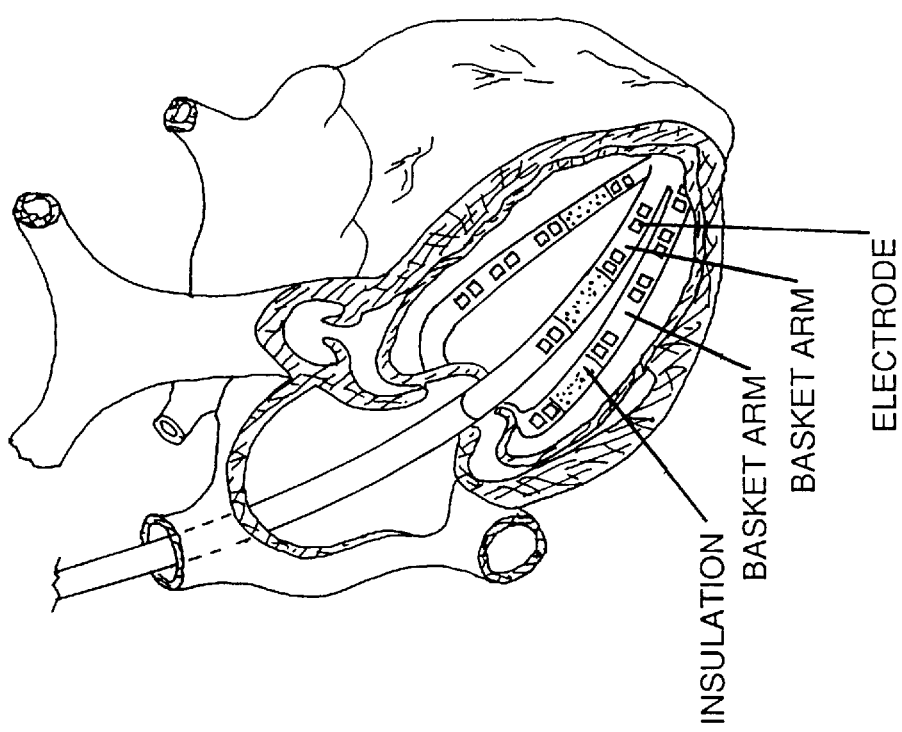
FIG. 3.
Figure 4:
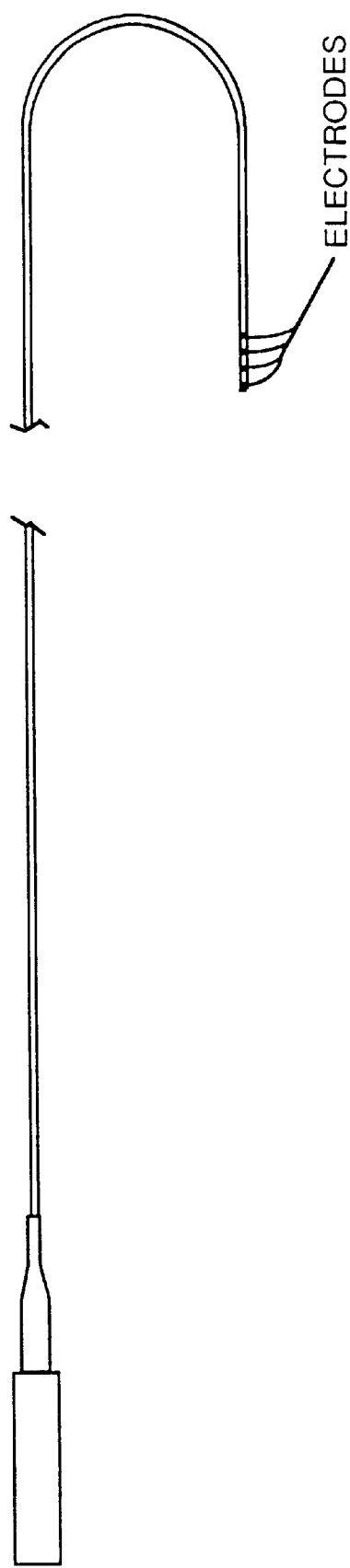
FIG. 4.
Figure 5:
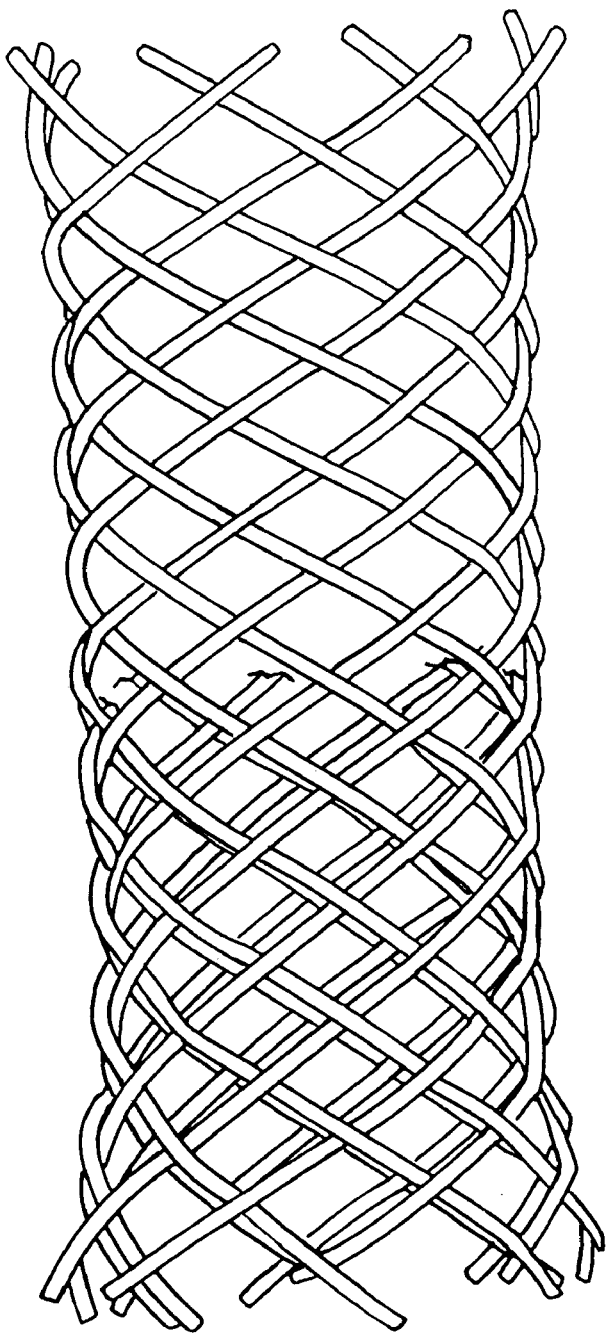
FIG. 5.
Figure 6:
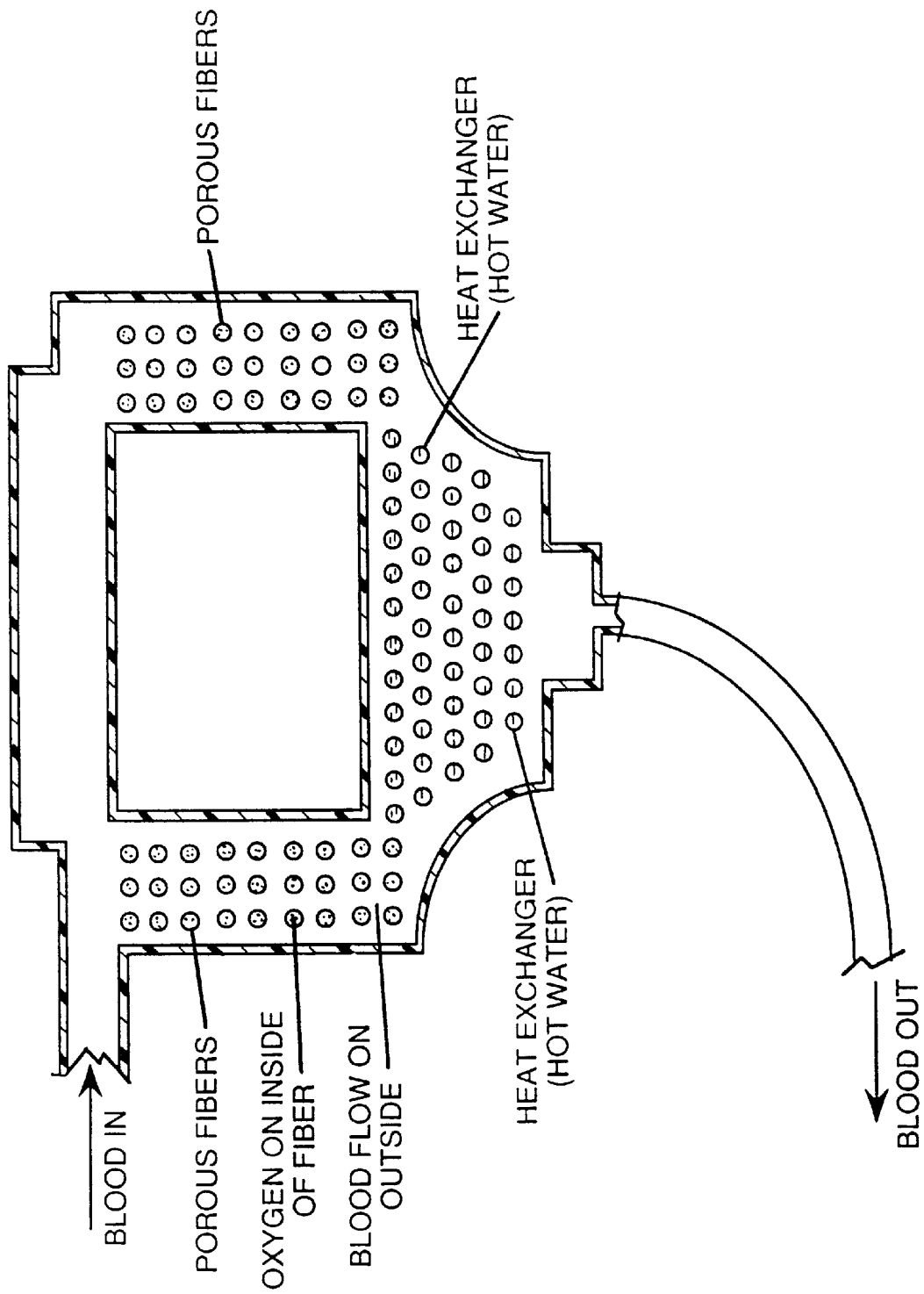
FIG. 6.

The invention provides a wide variety of covalently attached biocompatible coatings for surfaces of medical devices. In particular embodiments, the invention provides covalently attached antithrombogenic coatings for medical device surfaces exposed to blood flow and thrombogenic coatings for medical device surfaces not exposed to blood flow continuous with bodily circulation. The invention provides a variety of methods for making medical devices with such coatings.

The methods involve functionalizing the selected surface of a medical device with covalently bound reactive groups. The surface is further contacted with a bioactive agent, in particular an antithrombogenic agent, which is covalently coupled to the reactive group to form a coating effective to inhibit the formation of thrombus when the surface is exposed to blood flow continuous with bodily blood circulation. While described below primarily with antithrombogenic agents, it is understood that a wide variety of bioactive agents, e.g. antibiotics, may be substituted for the antithrombogenic agents, depending on the desired characteristics of the device's surface.

In one embodiment, the functionalizing step comprises contacting the surface with a plasma to form chemically reactive groups. The plasma used in this method is conveniently "low temperature" or "cold" plasma produced by glow discharge. A low temperature plasma is created in evacuated chamber refilled with a low pressure gas. The pressures are typically in the order of 0.1 to 10 torr and the gas is excited by electrical energy in the radio frequency range (RF). The glow discharge, typically in the range of 100 to 1,000 watts, depending on the chamber volume, contains ions, electrons, metastables, and photons. When these species interact with the surface a variety of reactions can take place. Bonds can be broken, new bonds are formed, and if a reactive gas is used this can also react with the substrate.

A wide variety of reactive groups which provide convenient reactants for the selected bioactive agent may be used. For example, hydroxyl groups are attached to the surface either with use of methane/oxygen plasma or water/oxygen plasma. A carboxyl rich surface is generated by the deposition of acrylic acid to the surface of the device. Frequently, the reactant is provided with a carrier gas; for example, methane gas which additionally provides surface polyalkyl (hydrocarbon) chains may be advantageously used where otherwise unreactive metal surfaces are to be coated. Alternatively, an inert carrier gas such as helium or argon may be used. Typically the gas/reactant are introduced in a ratio of approximately 3:1.

Device surfaces are typically treated for from about 0.5 to about 30 minutes, desirably obtaining a uniform distribution of amine on the plastic surface. The water surface tension of the modification may be confirmed by the water contact angle measurements.

The selected bioactive agent is covalently bound to the surface by thermochemical reaction with the surface reactive groups. For example, carboxyl groups readily react with xylose moieties on heparin in the presence of 1-(3-Dimethylaminopropyl)-3-ethylcarbodiimide, EDC, to form an ester linkage. Hirudin and its analogs are conveniently bound to a carboxyl rich surface by introduction of a specifically engineered amino group at the carboxyl terminus of the peptide away from the active amino terminus.

In another embodiment, the functionalizing step comprises contacting the surface with a self-aligned Langmuir-Blodgett film comprising an amphipathic compound and a bioactive agent. A crosslinking agent is then used to covalently crosslink the Langmuir-Blodgett film to the medical device surface and to the bioactive agent. For example, an argon or helium plasma chamber is used to contact the Langmuir-Blodgett film-coated surface with high energy photons and electrons capable of chemically crosslinking the amphipathic compound and the bioactive agent. The amphipathic compound and bioactive agent may be applied sequentially or simultaneously. Similarly, the surface-amphipathic compound crosslinking and amphipathic compound-bioactive agent crosslinking may be performed either sequentially or simultaneously. Optionally, in this embodiment, the surface may also be functionalized with a first reactive group capable of reacting with at least one of the amphipathic compound and the bioactive agent. Similarly, the bioactive agent may be derivatized with a second reactive group capable of reacting with the first reactive group.

In these methods, the bioactive agent is advantageously derivatized with a label, particularly a fluorescent or colorimetric label, capable of providing a detectable signal. Hence the detectable signal is used to quantify the bound bioactive agent on the device's surface.

Where an antithrombogenic agent is used, it may be a relatively irreversible thrombin inhibitor, such as D-Phe-Pro-Arg-chloromethyl ketone, or a relatively reversible thrombin inhibitor, such as heparin or a polypeptide comprising the amino acid sequence Ile-Pro-Glu-Glu-Tyr-Leu-Gln. Prothrombogenic agents include thromboplastin, thrombocytin, and other clotting factors. Other useful bioactive agents include antimicrobial and antifungal agents, growth factors, etc.

For antithrombogenic coatings, the medical device has a surface destined for contact with blood flow continuous in vessels in the human body with bodily blood circulation as distinguished from blood permanently removed from bodily circulation. Exemplary devices include catheters, particularly intracardial catheters, vascular stents and grafts and various blood transfer devices such as blood oxygenators, dialysis and plasmapheresis devices, etc. In a specific embodiment, the medical device is an intracardial catheter probe for introduction into a chamber of the heart, having proximal and distal extremities and comprising a flexible elongate tubular member having at least one lumen extending therethrough extending the length thereof and having a distal extremity, a plurality of longitudinally and radially spaced apart electrodes, expandable means secured to the distal portion of said flexible elongate tubular member and being movable between a contracted position and an expanded position, means for mounting said electrodes on said expandable means whereby when said expandable means is moved to the expanded position in the chamber of the heart the electrodes are moved into engagement with the wall forming the chamber of the heart, means coupled to the expandable means for moving said expandable means between said contracted and expanded positions, said expandable means including a plurality of plastic elements having surfaces exposed to the blood and said elements having spaces therebetween when in the expanded position through which the blood can flow, lead means for conducting electrical energy in contact with the electrodes and extending into said flexible elongate tubular member and electrical means connected to said lead means for performing electrical functions with respect to said electrodes.

Medical devices suitable for thrombogenic coatings include devices for occluding aneurisms or ruptured vessels, for closure of percutaneous or vascular puncture sites, etc. For example, the proximal end of the introducer of such devices as laparoscopes, catheters, etc. may also be advantageously so coated.

Many of the subject medical devices of the invention have a blood flow-contacting surface with a covalently attached dry coating to inhibit thrombosis. In one embodiment, the coating comprises reactive linking groups covalently bound to the surface and a bioactive agent covalently bound to a portion but fewer than all of the reactive linking groups. In another embodiment, the coating comprises a Langmuir-Blodgett film comprising an amphipathic compound and a bioactive agent, where the amphipathic compound is covalently crosslinked to the surface, and the bioactive agent is covalently crosslinked to the amphipathic compound.

The invention also provides general methods for treating a surface of a medical device to inhibit thrombosis which involve causing a bioactive agent to become covalently bound to a medical device surface exposed to blood flow continuous with bodily blood circulation; thereafter, washing the surface to remove any bioactive agent which is not covalently bound; thereafter, causing a reagent capable of selectively, non-covalently binding to the bioactive agent to become selectively and noncovalently bound to the bioactive agent; thereafter, washing the surface to remove any of such reagent which is not selectively bound to the bioactive agent; thereafter, detecting a radiative signal at an intensity which meets or exceeds a predetermined intensity which correlates with the presence of coating of a predetermined amount of the bioactive agent covalently bound to the surface. For example, the reagent may be a specific antibody and the signal fluorescence.

EXAMPLES

In a specific case, an antithrombogenic coating was applied to the surface of an electrophysiology catheter by this method. The catheter was made of PBax tubing loaded with barium salt. The distal end of the catheter had annular platinum electrodes and a platinum cap. First the catheter was placed in the plasma chamber and the chamber was evacuated. A mixture of methane (490 SCCM) and ammonia (161 SCCM) were introduce into the chamber maintained at 0.265 torr pressure. A 400 watts glow discharge was established between the electrodes. The sample was treated for 3 minutes under these conditions. Under these condition there was formed a uniform distribution of amine on the plastic surface. Between 40 to 100% of the surface is covered by amine groups. The modification was confirmed by the water contact angle measurements. The contact angle was 85 degrees for the untreated sample, the treated sample had a contact angle of 41 degrees.

The bioactive agent was derivatized when necessary to improve the covalent binding to the device. In case of heparin the xylose can be reacted with the carboxyl group on the plasma treated surface by simple esterification in the presence of 1-(3-Dimethylaminopropyl)-3-ethylcarbodiimide, EDC. 200 mg of EDC was dissolved in 5 ml of water and the pH was adjusted to 4 with dilute hydrochloric acid. The device was immersed in this solution. Heparin (200,000 units) dissolved in 5 ml of water was added to this. The pH was adjusted to 4 again. The solution was periodically stirred for two hours at room temperature. An additional 100 mg of EDC was added and the reaction continued for 12 hours. The device was then washed with phosphate buffered saline to remove unreacted heparin. The device was then air dried and stored moisture free.

The effectiveness of the coating was determined in vitro by blood clotting time. Citrated cow blood was incubated at 37° C. A heparin coated device was immersed in the blood. The clotting was initiated by the addition of 2–3 drops of 10% calcium chloride solution. Control tubes with no device and with an uncoated device were also maintained. The time for clot formation was determined by examining the test tube periodically. In the control test tube the clotting started in less then 15 minutes. Heparin coated devices prevented the clotting for at least 2 hours.

In vivo, studies were conducted in sheep. The coated device was introduced to left ventricle. After leaving the device in place for one hour the device was withdrawn. The device was gently rinsed in saline and the surface was examined for thrombus. With a good heparin coating very little or no thrombus formation was observed.

The stability of coating was determined by extracting the device in saline for 1 to 24 hours. at 37° C. and then performing the in vitro studies as described above. There was no substantial difference in the clotting times for the saline extracted devices. Nearly all the heparin is covalently bound to the device.

In another example, in a Langmuir-Blodgett trough, a laminar flow of water at 1 gallon/hr was established. At one end of the trough a solution of amphiphilic molecules in a water miscible solvent such as acetone is dispensed at a controlled rate. The amphiphilic molecules will spread on the surface of the water and form a film. If they are rodlike molecules they tend to align within this film. By controlling the dispensing rate of the amphiphile the thickness or the number of monolayers in the film can be controlled. When a device such as a catheter is immersed in the water and slowly withdrawn the film is transferred to the device surface. The film thus transferred can be dried on the surface to give a highly oriented coating. Additional layers of the coating can be applied by repeated dipping and drying. A multilayer coating can be annealed to get interpenetration of the layers. Langmuir-Blodgett films are not generally very stable. If a device coated with Langmuir-Blodgett film is subjected to plasma treatment covalent bonds can be generated between the rods and between the device and the film. Such a crosslinked coating is very robust. To a Langmuir-Blodgett trough with laminar water flow a solution of γ-methyl-L-glutamate-γ-n-octadecyl-L-glutamate copolymer is dispensed through a narrow slot just touching the water surface. The rate was controlled to attain a double layer of glutamate polymer. The film was transferred to a intercardial catheter made of polyethylene and gold sensing elements. The film was air dried at 45° degrees C. for 1 hr. This was then coated for a second time with a layer of hirudin derivatized at the carboxyl terminus with octadecyl-L-glutamate. The second bioactive layer was air dried as before. Then this device was placed in a plasma chamber and subjected to an argon glow discharge for 3 min. at 300 watt. The high energy particles induce high reactive free radicals within the Langmuir-Blodgett film. These radicals then covalently link the aligned film components as well as the film to the substrate. Poly (tetramethoxytetraoctoxyphthalocyanato) polysiloxane, isopentyl cellulose and butylcellulose are other examples of materials that are hairy rods that form nice Langmuir-Blodgett films. A variety of bioactive peptides can be derivatized to form self assembled films.

The device can be functionalized first with plasma to have a reactive function such as a carboxyl, hydroxyl, carbonyl or an amine group before Langmuir-Blodgett film deposition. This then can be subjected to a procedure as described above.

The Langmuir-Blodgett film layer can also be formed by a mixture of the rodlike amphipile and the derivatized biomolecule in a single dip process. This will give a coating of amphiphiles interspersed with bioactive molecules. This then can be covalently linked using inert gas plasma.

What is claimed is:

1. A medical device for use in a human body having vessels with blood circulating therein, said device comprising a body having a surface, said surface being treated by glow discharge in the absence of a reactive gas to provide a plurality of reactive functional groups on said surface and an antithrombogenc agent covalently and directly bound to a portion but fewer than all of said reactive groups on the surface to provide a coated surface which is effective to inhibit the formation of thrombus when said coated surface is exposed to blood.

2. A medical device according to claim 1 in the form of an intracardial catheter probe for introduction into a chamber of the heart defined by a wall in the human body having the vessels in communication with the heart comprising a flexible elongate tubular member having proximal and distal extremities and having at least one lumen extending therethrough extending the length thereof from the proximal extremity to the distal extremity, a plurality of longitudinally and radially spaced apart electrodes, expandable means secured to the distal extremity of said flexible elongate tubular member and being movable between a contracted position and an expanded position, means mounting said electrodes on said expandable means whereby when said expandable means is moved to the expanded position in the chamber of the heart the electrodes are moved into engagement with the wall of the chamber of the heart, means coupled to the expandable means for moving said expandable means between said contracted and expanded positions, said expandable means including a plurality of elements having surfaces exposed to the blood with spaces therebetween when in the expanded position through which the blood can flow, lead means connected to the electrodes and carried by said flexible elongate tubular member and electrical means connected to said lead means for performing electrical functions with respect to said electrodes and wherein said catheter probe has said surface with the dry coating adhered thereto exposed to the circulating blood and wherein said antithrombogenic agent is heparin.

3. A medical device for use in a human body having vessels with blood circulating therein, said device having a surface adapted to be exposed to the circulating blood, a dry coating adhered to said surface, said dry coating comprising a Langmuir-Blodgett film of an amphipathic compound covalently crosslinked to said surface and an antithrombogenic agent covalently crosslinked to said amphipathic compound whereby said coating is effective to inhibit the formation of thrombus when said surface is exposed to blood flow.

4. A medical device for use in a human body having a surface adapted to be placed in contact with the human body, said surface being treated by glow discharge in the absence of a relative gas to provide a dry coating, said dry coating comprising a plurality of reactive groups on said surface and a bioactive agent covalently and directly bound to a portion but fewer than all of said reactive groups whereby a therapeutic effect is created by the coating.

5. A medical device for use in a human body having a surface adapted to be placed in contact with the human body, a dry coating adhered to said surface, said dry coating comprising a Langmuir-Blodgett film of an amphipathic compound covalently crosslinked to said surface and a bioactive agent covalently crosslinked to said amphipathic compound whereby a therapeutic effect is created by said coating.

6. A device as in claim 3 wherein said coating also comprises a marker material capable of providing a detectable signal.

7. A device as in claim 6 wherein said marker material is a fluorescent material.

* * * * *